US006992773B1

(12) United States Patent
Bruce et al.

(10) Patent No.: US 6,992,773 B1
(45) Date of Patent: Jan. 31, 2006

(54) DUAL-DIFFERENTIAL INTERFEROMETRY FOR SILICON DEVICE DAMAGE DETECTION

(75) Inventors: Michael R. Bruce, Austin, TX (US); Rama R. Goruganthu, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 446 days.

(21) Appl. No.: 09/386,112

(22) Filed: Aug. 30, 1999

(51) Int. Cl.
*G01B 9/02* (2006.01)
(52) U.S. Cl. ................................... 356/450
(58) Field of Classification Search ............... 356/450, 356/491, 237.2, 237.5
See application file for complete search history.

(56) References Cited

U.S. PATENT DOCUMENTS

| 5,737,072 A | 4/1998 | Emery et al. |
| 5,784,163 A | 7/1998 | Lu et al. |
| 5,866,436 A | 2/1999 | Miller |
| 5,880,838 A | 3/1999 | Marx et al. |

OTHER PUBLICATIONS

T.R. Corle and G.S. Kino, "Confocal Scanning Optical Microscopy and Related Imaging Systems," Phase-Contrast Imaging in the CSOM, Academic Press, 1996, pp. 232-233.

Slayter, Elizabeth M., and Slayter, Henry S., *Light and electron microscopy*, Cambridge University Press, 1992, pp. 153-158.

Meyer-Arendt, Jrgen R., *Introduction to Classical and Modern Optics*, Prentice Hall, 1972, pp. 211-212.

Rubbi, C.P., *Light Microscopy: Essential Data*, BIOS Scientific Publishers Limited, 1994, John Wiley & Sons, 1994, pp. 17-19.

*Handbook of Biological Confocal Microscopy*, edited by James B. Pawley, Plenum Press, New York, 1995, pp. 480-481.

Inoue S., and Spring, K.R., *Video Microscopy: The Fundamentals*, Second Edition, Plenum Press, New York, 1997, pp. 86-91.

*Primary Examiner*—Samuel A. Turner

(57) ABSTRACT

According to one aspect of the disclosure and a particular example application directed to a flip-chip packaged die, a method for detecting a defect in a surface of the die includes directing light through a first beam splitter; directing light of a known wavelength at the beam splitter, wherein the first beam splitter is adapted to direct a first beam of light into the back side of the semiconductor die which reflects a second beam of light back; and redirecting the second beam to a second beam splitter, the second beam splitter generating third and fourth beams of light. Analysis of the third and fourth beams of light is then performed, and this analysis can include using detectors in respective paths of the third and fourth beams of light to generate an arrival time differential and then comparing the differential with a reference previously generated using a nondefective die.

6 Claims, 2 Drawing Sheets

DUAL-DIFFERENTIAL INTERFEROMETRY FOR SILICON DEVICE DAMAGE DETECTION

FIELD OF THE INVENTION

The invention relates to semiconductor device assemblies, and more particularly, to techniques for analyzing and debugging circuitry from the back side that is opposite a circuit side of a die, for example, as with multi-layer, flip-chip integrated circuits.

BACKGROUND OF THE INVENTION

The semiconductor industry has seen tremendous advances in technology that has permitted dramatic increases in circuit density and complexity, and equally dramatic decreases in power consumption and package sizes. Present semiconductor technology now permits single-chip microprocessors with many millions of transistors, operating at speeds of tens (or even hundreds) of MIPS (millions of instructions per second) to be packaged in relatively small, air-cooled semiconductor device packages. A by-product of such high-density and high functionality in semiconductor devices has been the demand for multiple layers of metal interconnects for routing signals to and from so many circuit devices, and increased numbers of external electrical connections to be present on the exterior of the die and on the exterior of the semiconductor packages, which receive the die, for connecting the packaged device to external systems such as a printed circuit board.

There have been a number of semiconductor dies and packaging types used to address these issues. Semiconductor devices that have multiple layers of metal signal-routing interconnects are often referred to as multi-layer devices. Multi-layer devices typically have two or more layers (or levels) of metal interconnects built up over the portion of the die having the active devices. At this "circuit" or "front" side of the die, where the transistors and other active circuitry are generally formed, is a very thin epitaxially-grown silicon layer on a single crystal silicon wafer from which the die is singulated. The circuit side of the die is positioned very near the package, and opposes the backside of the die. The substrate between the backside and the circuit side of the die is typically a bulk silicon, such as single crystalline silicon.

To increase the number of pad sites available for a die, especially for multi-layer type dies, various semiconductor packaging types have been developed. One increasingly popular packaging technique is called "controlled collapse chip connection" or "flip-chip" packaging. In this technology, the bonding pads are provided with metal (solder) bumps. The bonding pads need not be on the periphery of the die and hence are moved to the site nearest the transistors and other circuit devices formed in the die. As a result, the electrical path to the pad is shorter. Electrical connection to the package is made when the die is flipped over the package with corresponding bonding pads and soldered. Once a flip-chip die is attached to the package, the backside portion of the die remains exposed. As a result, the dies are often referred to as "flip-chip" devices. Each bump connects to a corresponding package inner lead. The packages that result are lower profile, have lower electrical resistance, and a shortened electrical path.

The output terminals of such packages vary depending on the package type. For example, some output terminals are ball-shaped conductive bump contacts (usually solder, or other similar conductive material), and they are typically disposed in a rectangular array. These packages are occasionally referred to as "Ball Grid Array" (BGA). Another type of package, commonly known as a "Pin Grid Array" (PGA) package, implements the output terminals as pins.

For a flip-chip device with multi-layer metals, accessing the circuitry via the exposed backside of the die can be difficult because the circuit side of the flip-chip die is not visible or accessible for viewing using optical or scanning electron microscopy. The circuitry under the substrate backside of the die is in a very thin layer (e.g., about 10 micrometers) of silicon buried under the bulk silicon (e.g., greater than 500 micrometers).

Although the circuit of the integrated circuit (IC) is buried under the bulk silicon (i.e., the single crystalline silicon), infrared (IR) microscopy is capable of imaging the circuit because silicon is relatively transparent in these wavelengths of the radiation. However, because of the absorption losses of IR radiation in silicon, it is generally required to thin the die to less than about 100 microns in order to view the circuit using IR microscopy. To illustrate this difficulty, on a die that is 725 microns thick, at least 625 microns of silicon must be removed (or thinned) before IR microscopy can be used.

For failure analysis, thinning a flip-chip bonded die to such degrees is time consuming, burdensome, overly complex, and can damage the underlying circuitry that is to be analyzed for potential defects. These issues can be better appreciated through a discussion of the following common approach for such thinning.

Typically, thinning is accomplished by first thinning the die across the whole die surface; this type of thinning is referred to as "global thinning." Mechanical polishing is one method for global thinning. Once an area is identified as an area of interest and it is determined that access is needed to a particular area of the circuit, local thinning techniques can be used to thin an area smaller than the die size.

Focused ion-beam (FIB) milling is commonly used for thinning the backside of dice to permit e-beam signal acquisition to determine voltage levels of the nodes (e.g., to the millivolt level) while the part is actually operating. FIB milling is effective because it permits for local thinning to expose and/or access target circuitry nondestructively. For flip-chip multi-layer metal devices with advanced processes to expose the lower level metal nodes, the local thinning is implemented by milling deep, narrow holes through the backside of the die. For effective e-beam signal acquisition, the depth of the FIB hole should increase with its width. The ideal aspect ratio (depth to width) of a FIB hole is one to one. For a typical flip-chip having a relatively thick bulk silicon region between the backside and the circuit side of the die, the thickness of FIB holes must have an aspect ratio of about five to one. With this degree of aspect ratio, e-beam signal acquisition is very difficult.

Even when the circuitry is accessible via the type of imaging discussed above, certain defects are not always readily detected. For example, a particular attribute of semiconductor devices that requires testing is the integrity of the device substrate at the substrate surface. During manufacture and processing, the crystalline structure of semiconductor device substrate often becomes damaged. When materials are implanted in the device during operations such as ion implantation, the ions strike the device substrate and lose their energy via electronic and nuclear collisions. If the transferred energy during a nuclear collision is high enough, the atoms are displaced from their lattice sites in the crystalline structure, damaging the substrate. The magnitude of the damage increases as the energy transferred during a collision increases. Damage can also occur during postprocessing circuit usage; such damage includes, for example, CMOS latch-up events.

Damaged substrate results in reduced mobility in the damaged regions and defect levels in the band gap of the material, including deep-level traps for both electrons and holes, which have a tendency to capture free carriers from the conduction and valence bands. In addition to damaged crystalline structure, other abnormalities in the semiconductor devices may exist, for example, in the form of impurities in the substrate. If not repaired, the damaged regions may exhibit problems such as high resistivity.

As the semiconductor industry continues to demand increasingly complex and numerous manufacturing processes, the tendency for defects to occur within the substrate increases. Therefore, it would be helpful to have the ability to efficiently test structure within the semiconductor substrate to detect substrate surface damage.

SUMMARY OF THE INVENTION

According to one example embodiment, the backside of a semiconductor device, such as a flip-chip die of a semiconductor device, is analyzed to determine whether there is a defect in a surface within the die. In particular embodiments, interferometry techniques, such as dual-differential detection, are used to optically profile the surface of a die under analysis.

In a more particular embodiment also for a semiconductor device that includes a semiconductor die having a circuit side and bulk silicon in an back side opposite the circuit side, a method for detecting a defect at a surface in the die includes directing light through a first beam splitter; directing light of a known wavelength at the beam splitter, wherein the first beam splitter is adapted to direct a first beam of light into the back side of the semiconductor die which reflects a second beam of light back; and redirecting the second beam to a second beam splitter, the second beam splitter generating third and fourth beams of light. Analysis of the third and fourth beams of light is then performed, and this analysis can include using detectors in respective paths of the third and fourth beams of light to generate an arrival time differential and then comparing the differential with a reference previously generated using a nondefective die.

Other aspect of the present invention are directed to systems for implementing processes relating to the above-characterized method and to more specific methods and tools involved in such systems and processes.

The above summary is not intended to describe each illustrated embodiment or every implementation of the present invention. The figures and the detailed description which follow more particularly exemplify these embodiments.

BRIEF DESCRIPTION OF THE DRAWINGS

The following detailed description can best be understood when read in conjunction with the following drawings, in which.

Figure 1:
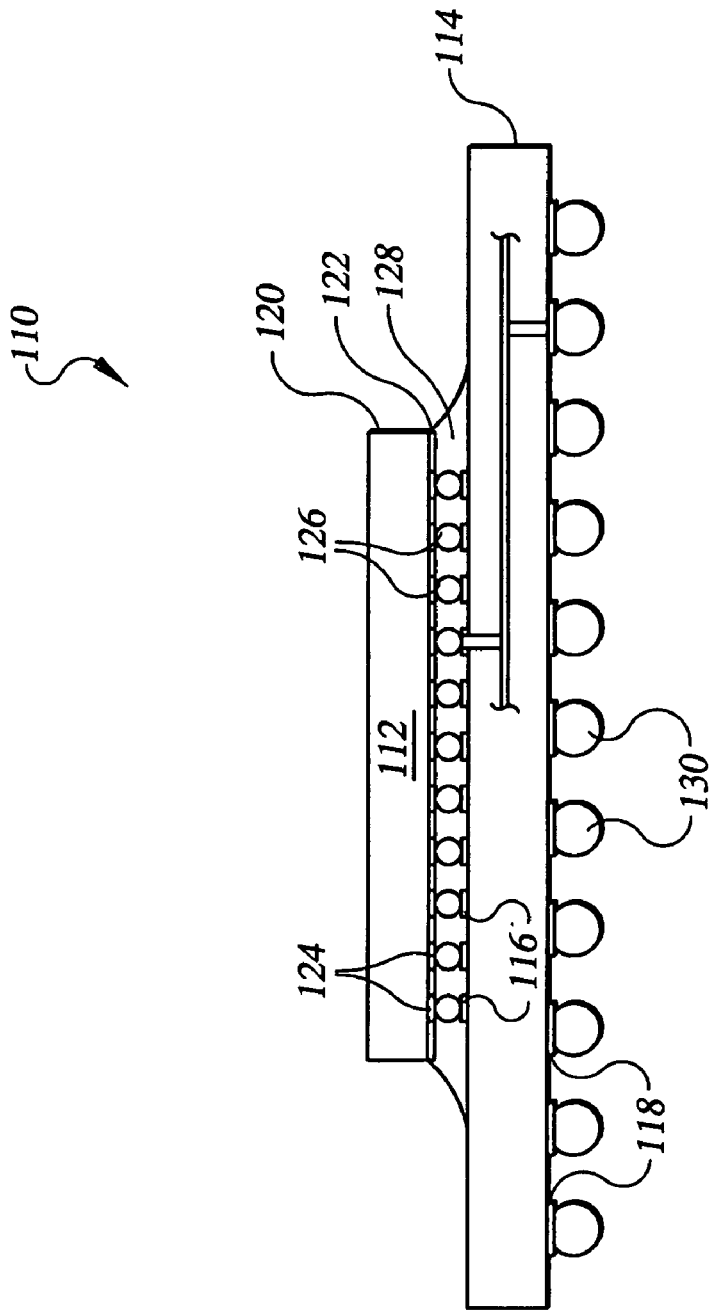
FIG. 1 shows a side view of a conventional integrated circuit packaged as a flip-chip device.

While the invention is amenable to various modifications and alternative forms, specifics thereof have been shown by way of example in the drawings and will be described in detail. It should be understood, however, that the intention is not to limit the invention to the particular embodiment described. On the contrary, the invention is to cover all modifications, equivalents, and alternatives falling within the spirit and scope of the invention as defined by the appended claims.

DETAILED DESCRIPTION

The present invention is believed to be applicable to a variety of different types of semiconductor devices, and the invention has been found to be particularly suited for failure analysis of flip-chip type circuit packages. While the present invention is not necessarily limited to flip-chip type circuit packages, an appreciation of various aspects of the invention is best gained through a discussion of examples in such an environment.

According to a particular example embodiment of the present invention, a conventional die, such as the die of a flip-chip type device, is tested after globally thinning the backside of a semiconductor device so as to provide a remaining thickness of bulk silicon in the back side. The backside of a semiconductor device (also referred to as a die or integrated circuit) can be thinned, for example, to about 20 microns (more or less is also acceptable), using chemical-mechanical polishing, laser-etching, ion bombardment or another suitable technique. A possible defect in a surface of the die is then investigated using a method that includes directing light through a pair of beam splitters which are used to create a differential of two beams of light one of which is directed into the back side of the semiconductor die and reflected by a surface therein for evaluation along with the nonreflected beam. The reflected and nonreflected beams are analyzed to determine if there is a surface defect. The analysis can include comparing the beams of light with a reference previously generated using a similar method on a nondefective die.

FIG. 1 shows a side view 110 of one type of conventional flip-chip type die 112 assembled to a package substrate 114. Flip-chip die 112 has a backside 120 and a circuit side in a portion of the die known as the epitaxial layer 122. The epitaxial layer 122 includes a number of circuit devices and has a thickness in the range of one to fifteen microns. Bulk silicon fills the backside 120 and is referred to as the bulk silicon layer. A plurality of solder bumps 126 are made on the circuit side at pads 124. The solder bumps 126 are the inputs and outputs to the circuitry associated with the flip-chip type die 112. The flip-chip type die 112 is attached to the package substrate 114 via the solder bumps on the die 112. The package substrate 114 includes pads 116 that are arranged to correspond to the pattern of solder bumps 126 on the die 112. The region between the die 112 and package substrate 114 is filled with an under-fill material 128 that encapsulates the solder bump connections and provides additional mechanical benefits. The pads 116 are coupled via circuitry to pads 118 on the package substrate, and solder bumps 130 are formed on the pads 118. The solder bumps 130 are the inputs and outputs to the circuitry associated with the package substrate 114.

For a flip-chip type die such as die 112 of FIG. 1, failure analysis is usually accomplished by first using a global and/or local thinning process. Example implementations for such thinning include: mechanically polishing; laser-microchemically etching; and local thinning via ion bombardment, for example, using a focused ion beam (FIB) system such as an FC-type FIB system available from Micrion, Inc. of Peabody, Mass. This type of system is particularly advantageous, because it can be used to complete various aspects of process embodiments according to the present invention. These aspects include, for example, etching, navigation and measurements via the system's built-in IR microscopy.

Figure 2:
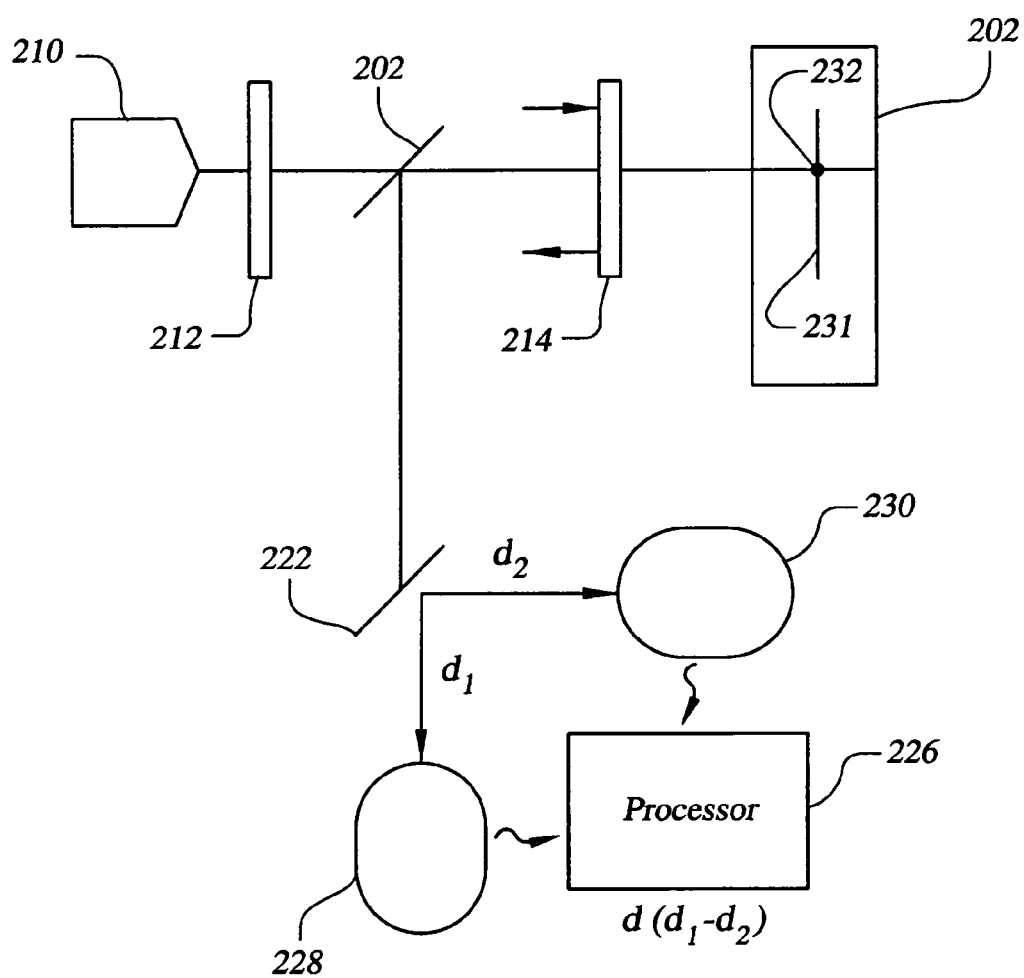
FIG. 2 shows a system for detecting a surface defect in the integrated circuit of FIG. 1 via a backside of the flip-chip die, according to the present invention.

According to the present invention, FIG. 2 illustrates an example system, using commercially available components, for detecting a surface defect in a flip-chip die 202 of the type shown in FIG. 1, with the analysis conducted via the backside of the die. This example system includes a near infrared laser 210, such as a YAG:nIR type laser, a linear polarizer 212, a ½ waveplate 214, a pair of beam splitters 220 and 222 and an nIR analyzer 226 that is responsive to detectors 228 and 230. The beam splitters 220 and 222 can be implemented using, respectively, a polarizer-type beam splitter (such as model 03PBS067 customized for nIR) and a 50/50 cube beam splitter for nIR (such as model 03BSC029), both available from Melles Griot, Inc.). The linear polarizer 212 can be implemented using PN 03FPI003 also available from Melles Griot, and the ½ waveplate 214 can be implemented using PN QWPO-1064-10-2-R15, available from CVI Laser, Corp. The nIR analyzer 226 is also conventional and can be implemented using equipment available from manufacturers, such as Melles Griot, Edmunds Scientific, Inc., CVI Laser and the like.

The system of FIG. 2 is used first to generate a reference profile for a designated surface in a nondefective die, referred to respectively as the "reference die" and the "reference surface." Accordingly, the first beam splitter 220 is positioned between the reference die and the laser 210. The laser 210 is used to direct light of a known wavelength through the first beam splitter 220, with the first beam splitter 220 adapted redirect the light that is reflected by the surface 231 under evaluation within the die 202. The redirected light that is reflected by the surface 231 is received and split into two corresponding beams of light for detection by the detectors 228 and 230. The nIR analyzer 226 receives the two corresponding beams of light reflected from the reference die, via the detector 228, and generates a profile for the reference surface, for example, by determining the time-arrival differential and/or the intensity difference for the two beams. For further information discussing the characterization and analysis of these profiles, reference may be made to a text entitled, *Confocal Scanning Optical Microscopy and Related Imaging Systems*, by T.R. Corle and G.S. Kino.

The above-characterized profile is then used as a reference against which other dies (of type and possibly manufacturing lot) under evaluation are compared for the detection of defects. For example, a die having a possible defect at this surface level can then be evaluated by conducting a similar method; the system of FIG. 2 is used with the reference die replaced with the die being evaluated. A profile for the die being evaluated is generated and compared to the previously-generated profile. Using dual-differential detection as described above, a defect, depicted as 232 in FIG. 2, is detected by the defective surface generating an optical path time/wavelength differential that is different from the optical path time/wavelength differential profiled in connection with development of the reference from the reference die.

In particular example embodiments, the reflecting surface is the transition in substances from one material to another material (such as from an epitaxial silicon region to an oxide), the reflecting surface is a defect in one material type (such as within a well region), and the reflecting surface is transition from one concentration of doped silicon to another concentration of doped silicon (such as from a p+ epitaxial silicon to an active or well region). In various testing applications of a flip-chip die, reflecting surfaces of these example types are tested to detect defects including but not limited to: contaminants such as potassium deposits, fractures in the silicon, various crystal defects, particulates and dopants. For such defects, the optical path difference profiled in connection with development of the reference can be readily distinguished from the optical path difference profiled in connection with die under evaluation, for example, by examining shifts in intensity.

The present invention is amenable to various modifications and alternative forms that depart from the particular embodiments described above. The invention is to cover modifications, equivalents, and alternatives falling within the spirit and scope of the invention as defined by the appended claims.

What is claimed is:

1. For a semiconductor device that includes a semiconductor die having a circuit side and bulk silicon in a back side opposite the circuit side, a method for detecting a defect at a surface in the die, comprising:

locating a first beam splitter for optical manipulation relative to the back side of the semiconductor die;

directing light of a known wavelength at the beam splitter, wherein the first beam splitter is adapted to direct a first beam of light into the back side of the semiconductor die which reflects a second beam of light back to the first beam splitter;

redirecting the second beam to a second beam splitter, the second beam splitter generating third and fourth beams of light;

analyzing the third and fourth beams of light, including comparing a relational factor that is a function of the two beams of light and is a function of a time differential, or intensity, between the third and fourth beams of light with a reference and detecting therefrom a surface defect in the die; and using the first and second beam splitters to generate different third and fourth beams from a nondefective semiconductor and analyzing the different third and fourth beams of light to develop the reference.

2. A method, according to claim 1, further including thinning the back side of the die before the steps of claim 1.

3. A method, according to claim 2, wherein thinning the back side of the die includes locally thinning a portion of the back side of the die.

4. A method, according to claim 2, wherein thinning the back side of the die includes locally thinning a portion of the back side of the die to a thickness of less than about 20 microns.

5. For a semiconductor device that includes a semiconductor die having a circuit side and bulk silicon in a back side opposite the circuit side, a method, for detecting a defect at a surface in the die, comprising:

locating a first beam splitter for optical manipulation relative to the back side of the semiconductor die;

directing light of a known wavelength at the beam splitter, wherein the first beam splitter is adapted to direct a first beam of light into the back side of the semiconductor die which reflects a second beam of light back;

redirecting the second beam to a second beam splitter, the second beam splitter generating third and fourth beams of light; and analyzing the third and fourth beams of light, including comparing a relational factor that is a function of the two beams of light and is a function of a time differential, or intensity, between the third and fourth beams of light with a reference and detecting therefrom a surface defect in the die.

6. A system for detecting a defect in a semiconductor device that includes a semiconductor die having a circuit side and bulk silicon in a back side opposite the circuit side, comprising:
- a first beam splitter adapted for optical manipulation relative to the back side of the semiconductor die;
- a laser for directing light of a known wavelength at the first beam splitter, wherein the first beam splitter is adapted to direct a first beam of light into the back side of the semiconductor die which reflects a second beam of light back;
- a second beam splitter for generating third and fourth beams of light in response to the second beam being a redirected; and
- a processor adapted for analyzing the third and fourth beams of light, including comparing a relational factor that is a function of the two beams of light and is a function of a time differential, or intensity, between the third and fourth beams of light with a reference and detecting therefrom a surface defect in the die.

* * * * *